US010254224B2

(12) United States Patent
Bolduc et al.

(10) Patent No.: US 10,254,224 B2
(45) Date of Patent: Apr. 9, 2019

(54) HANDHELD FLUOROMETER

(71) Applicant: Ecolab USA Inc., St. Paul, MN (US)

(72) Inventors: John Wilhelm Bolduc, Inver Grove Heights, MN (US); Justin Scott Valenstein, Eagan, MN (US); Amanda Bakken, Eagan, MN (US); Stacy Fawbush, St. Paul, MN (US); Jeffrey Hutchison, St. Paul, MN (US); Eugene Tokhtuev, Duluth, MN (US); Anatoly Skirda, Hermantown, MN (US); Anna Pilipchenko, Duluth, MN (US)

(73) Assignee: Ecolab USA Inc., Saint Paul, MN (US)

(*) Notice: Subject to any disclaimer, the term of this patent is extended or adjusted under 35 U.S.C. 154(b) by 295 days.

(21) Appl. No.: 14/970,573

(22) Filed: Dec. 16, 2015

(65) Prior Publication Data

US 2016/0097721 A1 Apr. 7, 2016

Related U.S. Application Data

(63) Continuation of application No. 14/457,573, filed on Aug. 12, 2014.

(51) Int. Cl.
G01N 21/64 (2006.01)
G01N 21/85 (2006.01)
G01N 21/88 (2006.01)

(52) U.S. Cl.
CPC ........ *G01N 21/645* (2013.01); *G01N 21/6428* (2013.01); *G01N 21/8507* (2013.01);
(Continued)

(58) Field of Classification Search
CPC .................................................. G01N 21/645
See application file for complete search history.

(56) References Cited

U.S. PATENT DOCUMENTS 4,309,093 A 1/1982 Kuwayama et al.
4,783,314 A 11/1988 Hoots et al.
(Continued)

FOREIGN PATENT DOCUMENTS

WO 0135079 A1 5/2001
WO 2009007888 A1 1/2009

OTHER PUBLICATIONS

Miller et al., "Spectrofluorometric Determination of Calcium and Lanthanide Elements in Dilute Solution," Anal. Chem. 1982, vol. 54, p. 2022-2025.*

(Continued)

*Primary Examiner* — Yara B Green
(74) *Attorney, Agent, or Firm* — Fredrikson & Byron, P.A.

(57) ABSTRACT

A method of detecting concentration of dipicolinic acid and terbium chloride in a chemical composition with a fluorometer, wherein the fluorometer comprises an excitation source for emitting electromagnetic radiation at one or more wavelengths, and a detector module for detecting fluorescence emitted by dipicolinic acid, emitting electromagnetic radiation from the excitation source at wavelengths that induce fluorescence in dipicolinic acid-terbium chloride combination present in the chemical composition, detecting the fluorescence emitted by the dipicolinic acid-terbium chloride combination via the detector module, and determining the concentration of dipicolinic acid using predetermined relationship between fluorescence emitted and the concentration of dipicolinic acid-terbium chloride combination.

20 Claims, 13 Drawing Sheets

(52) U.S. Cl.
CPC . *G01N 21/8806* (2013.01); *G01N 2021/6471* (2013.01); *G01N 2201/068* (2013.01)

(56) References Cited

U.S. PATENT DOCUMENTS

| | | | |
|---|---|---|---|
| 4,802,768 | A | 2/1989 | Gifford et al. |
| 4,977,325 | A | 12/1990 | Bowen et al. |
| 5,208,466 | A | 5/1993 | Pentoney, Jr. et al. |
| 5,876,960 | A | 3/1999 | Rosen |
| 6,255,118 | B1 | 7/2001 | Alfano et al. |
| 6,369,894 | B1 | 4/2002 | Rasimas et al. |
| 6,402,986 | B1 | 6/2002 | Jones, II et al. |
| 6,831,745 | B2 | 12/2004 | Marquardt et al. |
| 6,842,243 | B2 | 1/2005 | Tokhtuev et al. |
| 7,095,500 | B2 | 8/2006 | Banks |
| 7,179,384 | B2 | 2/2007 | Moriarty et al. |
| 7,198,755 | B2 | 4/2007 | Tokhtuev et al. |
| 7,220,382 | B2 | 5/2007 | Godfrey et al. |
| 7,301,158 | B1 | 11/2007 | Hoang |
| 7,306,930 | B2 | 12/2007 | Ponce et al. |
| 7,563,615 | B2 | 7/2009 | Ponce |
| 7,611,862 | B2 | 11/2009 | Ponce |
| 8,038,947 | B2 | 10/2011 | Thompson |
| 8,173,359 | B2 | 5/2012 | Ponce et al. |
| 8,269,193 | B2 | 9/2012 | Christensen et al. |
| 2004/0080723 | A1 | 4/2004 | Inamoto |
| 2008/0030712 | A1* | 2/2008 | Tokhtuev ........... G01N 21/6402 356/51 |
| 2008/0252954 | A1 | 10/2008 | Wang et al. |
| 2009/0046756 | A1 | 2/2009 | Wang et al. |
| 2009/0159803 | A1 | 6/2009 | Berthold et al. |
| 2009/0220045 | A1 | 9/2009 | Grodzins |
| 2009/0283698 | A1 | 11/2009 | Chapman |
| 2011/0127444 | A1 | 6/2011 | Ozasa et al. |
| 2011/0142200 | A1 | 6/2011 | Piorek et al. |
| 2011/0246118 | A1 | 10/2011 | Tokhtuev et al. |
| 2012/0322166 | A1 | 12/2012 | Ohtsuka |
| 2013/0130272 | A1 | 5/2013 | Aojula et al. |
| 2013/0224850 | A1 | 8/2013 | Meyers et al. |

OTHER PUBLICATIONS

Barela et al., "A Simple, One-Step Fluorometric Method for Determination of Nanomolar Concentrations of Terbium," Anal. Chem. 1976, vol. 71, p. 351-357.*

Hindle et al., "Dipicolinic acid (DPA) assay revisited and appraised for spore detection," Analyst. Nov. 1999; 124, (11): 1599-604. PubMed PMID: 10746319.

Smith et al., "In situ surface-etched bacterial spore detection using dipicolinic acid-europium-silica nanoparticle bioreporters"; Appl Spectrosc. Aug. 2011; 65(8):866-75. doi: 10.1366/10-06167. PubMed PMID: 21819776.

International Patent Application No. PCT/US2015/043384, International Search Report and Written Opinion dated Oct. 28, 2015, 11 pages.

Rosen et al., "Bacterial Spore Detection and Determination by Use of Terbium Dipicolinate Photoluminescence," Anal. Chem., vol. 69, 1997, pp. 1082-1085.

European Patent Application No. 15832275, Extended European Search Report dated Mar. 29, 2018, 13 pages.

* cited by examiner

HANDHELD FLUOROMETER

CROSS-REFERENCES

This application is a continuation of U.S. application Ser. No. 14/457,573, filed Aug. 12, 2014, the content of which is hereby incorporated by reference in its entirety.

FIELD

This disclosure generally relates to systems and methods for measuring concentration of chemicals in a solution. More particularly, this disclosure relates to systems and methods involving a fluorometer for measuring concentration of chemicals in a solution.

BACKGROUND

Cleaning operations in public facilities such as restaurants, hotels, food and beverage plants, hospital, etc. typically uses a cleaning product having sanitizing, disinfecting and/or antimicrobial properties. Alternatively, certain chemical compound may be added to cleaning products to improve their chemical stability and/or shelf-life. For instance, dipicolinic acid can be added to certain cleaning products to improve their resistance to heat, thereby reducing the rate of degradation of the cleaning products when exposed to heat and extending the use of such cleaning products in regions with warm climates.

The concentration of dipicolinic acid may be measured in a number of situations. By measuring the concentration of dipicolinic acid, the concentration of microbial spores may be determined to comply with any regulatory standard. In another example, it may be necessary to maintain a certain concentration of dipicolinic acid to improve the stability of cleaning products. As dipicolinic acid exhibits fluorescence when excited by electromagnetic radiation of certain wavelengths, the concentration of dipicolinic acid in a solution can be measured by measuring the fluorescence of the solution. The intensity of fluorescence emitted by the solution may depend on the concentration of dipicolinic acid in the solution. For instance, the intensity of fluorescence emitted by the solution may be directly proportion to the concentration of dipicolinic acid. By measuring the intensity of the fluorescence emitted by dipicolinic acid, the concentration of dipicolinic acid can therefore be determined.

Fluorometers for measuring fluorescence of a sample are relatively well known. An exemplary fluorometer for measuring fluorescence is disclosed in U.S. Pat. No. 8,269,193 and U.S. Pat. No. 8,352,207 both assigned to Ecolab Inc., St. Paul, Minn., the disclosure of each of which is here by incorporated by reference in its entirety. Fluorometers generally have of a source of electromagnetic radiation that can excite a sample (e.g., dipicolinic acid solution of an unknown concentration), and a detector adapted to measure the intensity of fluorescence emitted by the electromagnetic radiation.

In many situations the concentration of a substance of interest in a solution (e.g., cleaning solution) may be low. For instance, regulatory requirements may necessitate that only a minimum level of the substance of interest (e.g., microbes) is present in a target area. In such cases, the intensity of fluorescence emitted by such substances of interest can be proportional to their concentration. Low concentrations (e.g., on the order of a few hundred parts per billion) may result in decrease in intensity of emitted fluorescence. For instance, the fluorescence may decrease directly proportional to the decrease in concentration (or by diluting the substance of interest). Typical fluorometers known in the art may not be able to measure such low levels of fluorescence with high accuracy and sensitivity.

SUMMARY OF THE INVENTION

Certain embodiments of the invention include a fluorometer for measuring fluorescence of a sample. The fluorometer can include a housing, a controller supported by the housing, and a sensor head. The sensor head can include an emitter module and a detector module operatively coupled to the controller. The emitter module can include an excitation source configured for emitting electromagnetic radiation at one or more wavelengths to induce fluorescence in the sample. The emission of the electromagnetic radiation can be directed along a first beam path. The sensor head can include an excitation filter for transmitting electromagnetic radiation within a first wavelength range toward the sample. The excitation filter can be supported by an excitation filter holder. The excitation filter holder can define an aperture for passage of electromagnetic radiation. The excitation filter holder can support the excitation filter such that the excitation filter permits passage of filtered electromagnetic radiation through the aperture and towards the sample such that the first beam path defines a trajectory of electromagnetic radiation from the excitation source to the excitation filter, via the aperture and toward the sample. The detector module can detect fluorescence emitted by the sample. The fluorometer displays the concentration of the substance in the sample determined by the controller, based on the measured fluorescence.

In some embodiments, the fluorometer includes a first focusing apparatus and a second focusing apparatus. The first focusing apparatus and the second focusing apparatus can be housed in the housing proximate the sensor head. The first focusing apparatus can direct electromagnetic radiation originating from the excitation source and transmitted by the excitation filter towards the sample. The second focusing apparatus can direct fluorescence originating from the sample toward the detector module.

In some embodiments, the aperture can be positioned asymmetrically relative to the first beam path such that the aperture passes an asymmetrical portion of the electromagnetic radiation in the first beam path and the excitation filter holder blocks passage of a corresponding asymmetrical portion of the electromagnetic radiation in the first beam path. The blocked passage of the corresponding asymmetrical portion of the electromagnetic radiation in the first beam path can reduce the amount of electromagnetic radiation oriented directly from the emitter module to the detector module. In some embodiments, the aperture is of semicircular cross-section. In some embodiments, the aperture is shaped by obstructing at least a portion of a circular opening. In some embodiments, the aperture is shaped to prevent electromagnetic radiation passing through the first focusing apparatus from being directed toward the second focusing apparatus.

The details of one or more embodiments of the invention are set forth in the accompanying drawings and the description below. Other features, objects, and advantages will be apparent from the description and drawings, and from the claims.

BRIEF DESCRIPTION OF THE DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
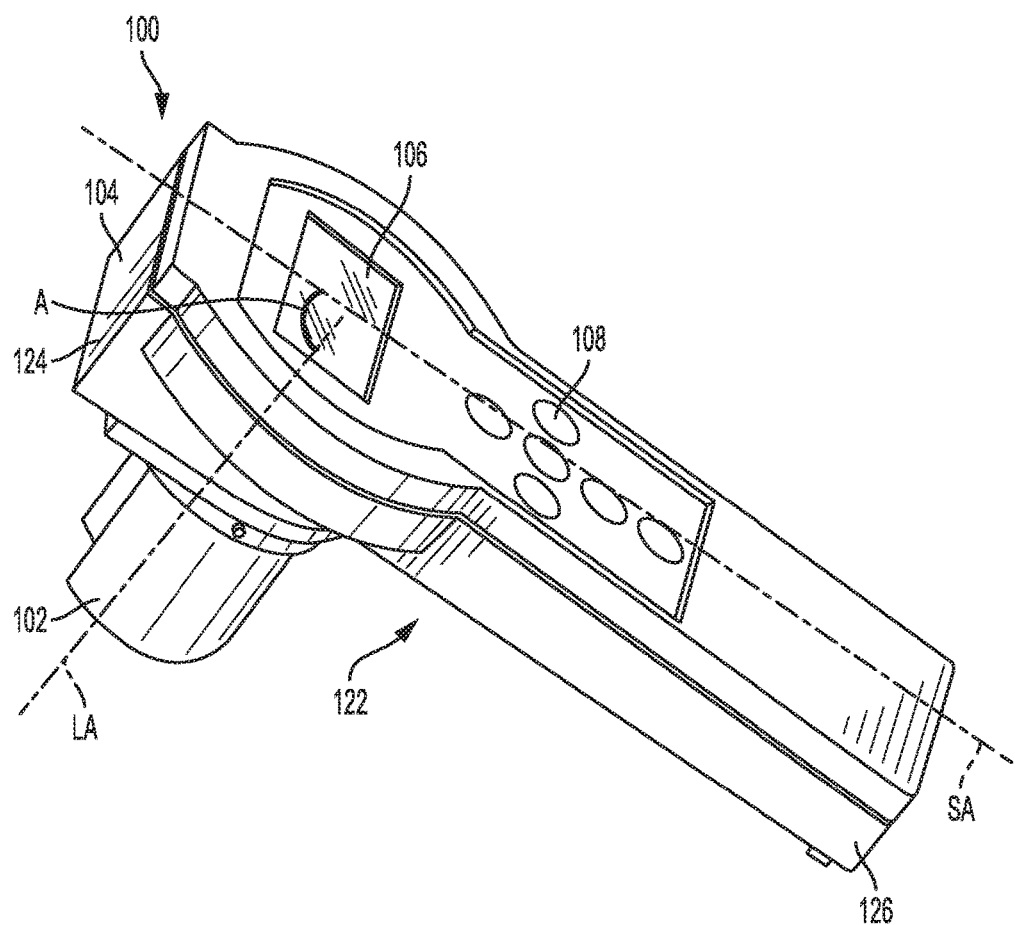
FIG. 1 is a perspective view of a fluorometer according to an embodiment of the invention.
Figure 2:
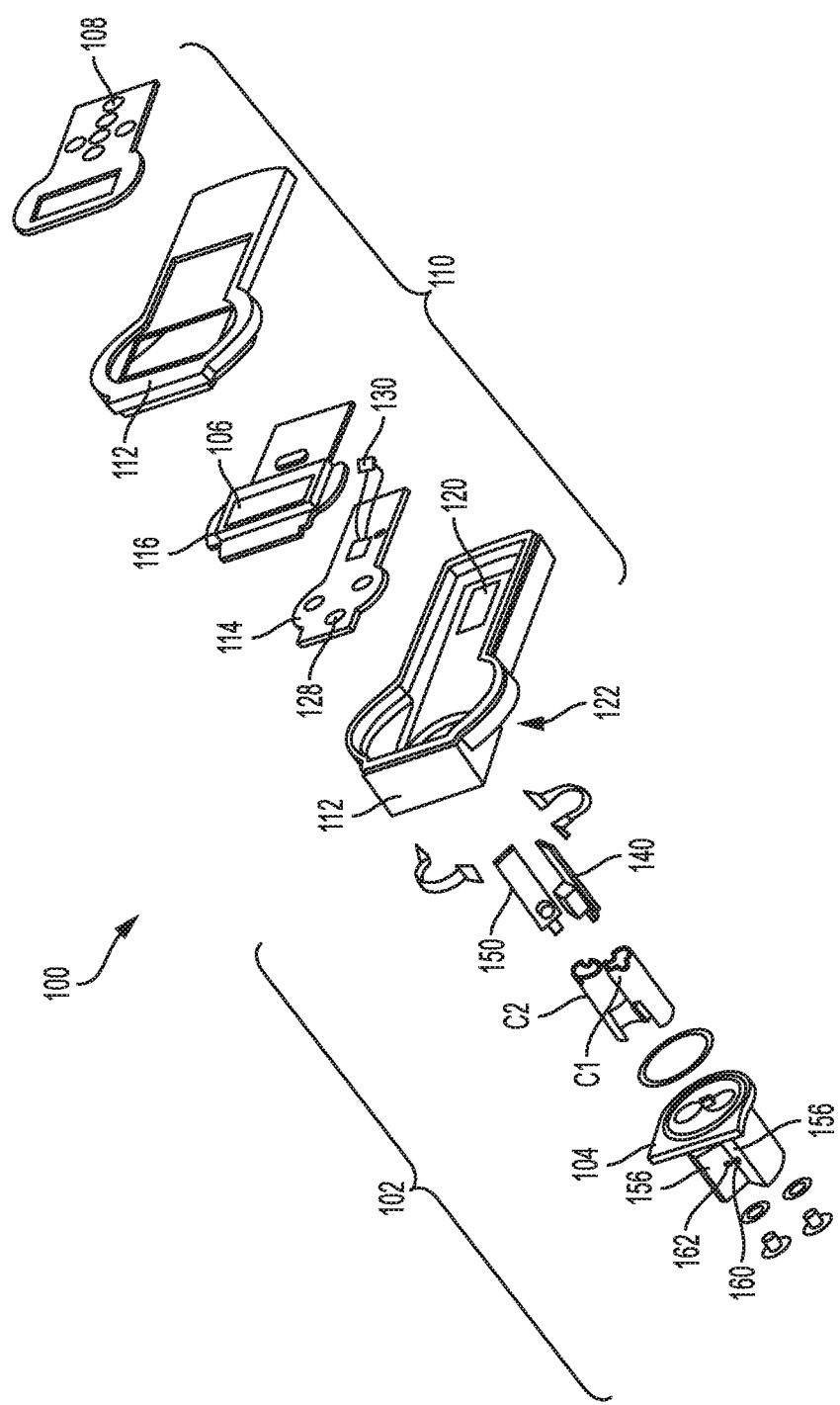
FIG. 2 is an exploded perspective view of the fluorometer of FIG. 1.

FIGS. 1 and 2 are perspective and exploded views, respectively, of a fluorometer 100 according to some embodiments of the invention. The fluorometer 100 can be useful for measuring fluorescence emitted by certain samples. Moreover, the fluorometer 100 can facilitate determining the concentration of certain samples in a solution based on the measured fluorescence. Such embodiments can be useful for measuring intensity of fluorescence emitted by samples such as dipicolinic acid and other chemicals (e.g., found in cleaning products). Based on the measured intensity of emitted fluorescence, the concentration of dipicolinic acid in a solution (e.g., a sanitizer, disinfectant, detergent, and the like) can be determined.

In general, the fluorometer 100 can measure intensity of fluorescent emission from a sample (e.g., a chemical solution, such as an antimicrobial or cleaning product) having a substance of interest (e.g., dipicolinic acid). The fluorometer 100 can calculate concentration of the substance in the sample, and display the determined concentration to a user. The user can then perform any desired actions based on the determined concentration, such as, for example, adding more of the substance in order to increase the concentration of the substance. If the fluorometer 100 determines that the concentration is lower or higher than a threshold concentration, the user can dispense more or less of the substance. Additionally, the fluorometer 100 can be operatively coupled to an out-of-product sensor. In certain embodiments, when the concentration of the substance is below a pre-determined threshold, the fluorescence emitted by the substance may be at a lower intensity. At this point, the out-of-product sensor can alert the user that the concentration of the substance has reached below a pre-determined threshold. The signal can be a visual, audio signal, or any other type of signal known in the art. Accordingly, the user can ensure that sufficient quantity and/or concentration of cleaning, antimicrobial, sanitizing and/or disinfecting solution, or other substances of interest is present to achieve the desired effect (cleanliness, reduction in microorganisms, heat resistance, product stability, lubrication, etc.).

The basic operation of a fluorometer 100 is well known, and accordingly, various details are omitted here for conciseness and clarity. The fluorometer 100 can calculate a concentration of a particular substance in a sample based on fluorescent properties of the substance. As will be described in more detail herein, the fluorometer 100 includes an excitation source 158 that emits electromagnetic radiation at one or more selected wavelengths, or continuously within a wavelength range. When the substance of interest is exposed to electromagnetic radiation at one or more selected wavelengths, (e.g., within a wavelength range), it may cause excitation of electrons in certain molecules of the substance and induce them to emit electromagnetic radiation. The emitted electromagnetic radiation can be of a different energy (i.e., at another wavelength range) from the electromagnetic radiation emitted by the excitation source 158. The electromagnetic radiation emitted by the substance can then be converted into an electrical signal. The electrical signal can indicate the intensity of fluorescent emissions. The concentration of the substance can then be determined based on a known relationship between the intensity of the fluorescent emissions and the concentration of the substance (e.g., via a calibration).

A number of variations and specific details of this general process are contemplated for embodiments of the invention involving fluorometers. In one example the concentration of water treatment products or solutions may be determined. In another example, the substance of interest may be any chemical solution. Examples include, but are not limited to, biocides such as pesticide and antimicrobial products, anti-corrosion, antiscaling, and antifouling products, disinfectants, and other cleaning products, detergents, additives, surfactants, lubricants, antimicrobial agents, solvents, hydrotropes, antiredeposition agents, dyes, corrosion inhibitors, acids, alkaline solutions, salt solutions, and bleaching additives. These compounds can be incorporated into products like ware-washing detergents, rinse aids, laundry detergents, clean-in-place cleaners, antimicrobials, floor coatings, meat, poultry and seafood carcass treatments, pesticides, vehicle care compositions, water care compositions, pool and spa compositions, aseptic packaging compositions, bottle washing compositions, and the like. Examples of some of these compounds and corresponding applications can be found in U.S. Pat. No. 7,550,746 assigned to the assignee of the instant application, the disclosure of which is herein incorporated by reference.

As seen in FIGS. 1 and 2, the fluorometer 100 includes a sensor head 102. The sensor head 102 can be made from a plastic and may be molded and/or milled to achieve the desired shape and features. The sensor head 102 includes a fluid-tight sensor head housing 104 (e.g., O-ring seals) that facilitates operation of the fluorometer 100 when partially or wholly immersed in a fluid sample of interest, and protects various components of the sensor head 102 from exposure to fluids. Accordingly, in some cases the sensor head 102 has some features and/or characteristics similar to an immersible dip probe. For example, in some embodiments of the invention the sensor head 102 has one or more features and/or components similar to those described in commonly-assigned U.S. Pat. No. 7,550,746, U.S. Pat. No. 7,652,267, U.S. Pat. No. 7,989,780, and U.S. Pat. No. 8,084,756 all assigned to the assignee of the instant application, the disclosure of each of which is hereby incorporated herein by reference. The sensor head 102 can be immersed into a sample container (not shown) to measure fluorescence and/or concentration. The fluorometer 100 also includes an electronic display 106 for displaying data (e.g., concentration, intensity), to a user, and an input interface in the form of the keypad 108 that allows the user to interact with the fluorometer 100 (e.g., saving measured concentration or intensity, setting parameters for measurement, viewing previously stored measurement data, etc.).

The sensor head 102 can be connected to a controller module 110. In some embodiments, the controller module 110 has a controller housing 112 which provides a convenient form, similar to a handle or wand, to easily grasp or hold the fluorometer 100 by hand. In some embodiments, the controller module 110 generally includes those components necessary to determine a concentration of a product based on a signal received from the sensor head 102. As shown in FIG. 2, the controller module 110 includes a controller board 114 that couples with a display board 116 via a display board cable. The display board 116 allows the electronic display 106 (e.g., an LCD screen) to display information (e.g., measured concentration, intensity of fluorescence) to a user. The controller module 110 also includes an input interface in the form of a keypad 108. The controller module 110 also includes a portable power source 120, (e.g., battery) for powering the fluorometer 100.

In some cases, the sensor head 102 is connected to (e.g., by fasteners or adhesives) or integral with a bottom surface 122 of the controller housing 112 opposite from the electronic display 106 and positioned proximate a distal end 124 of the controller housing 112. In some embodiments, the sensor head 102 housing is fixedly attached to the bottom surface 122 of the controller housing 112. In some embodiments, the sensor head housing 104 may be integrally formed with at least a portion of the controller housing 112. In one example, a user can grasp the controller housing 112 near a proximal end 126 of the controller housing 112 to take measurements from a sample. Additionally, the user can grasp the controller housing 112 near the proximal end 126 of the controller housing 112 to read the electronic display 106, and/or to manipulate the keypad 108. For example, a user may dip the sensor head 102 into a sample by holding the controller module 110 above the surface of a sample (e.g., in a reservoir, container, beaker, etc.) with the sensor head 102 partially or completely immersed in the sample. In some embodiments, a user may grasp the proximal end 126 of the controller module 110 while securing a sample container to the sensor head 102. Other configurations of the controller module 110 and the sensor head 102 are also possible.

Referring back to FIG. 2, the controller board 114 can have a number of discrete components positioned (e.g., soldered) and coupled together on a printed circuit board. The controller board 114 includes a controller 128, which calculates a concentration based on an intensity signal from the detector module 150. The controller 128 may provide a variety of other functions, including but not limited to, performing a calibration routine, accepting and executing instructions entered at the input interface, and/or formatting data for viewing on the fluorometer's electronic display 106. The controller 128 can be any of the controllers known in the art, such as a software driven microprocessor, a microcontroller, a field programmable gate array, an integrated circuit, and the like. In addition, the controller 128 or the controller board 114 may have on-board memory (not shown) that stores instructions for execution by the controller 128.

The controller board 114 also includes a power cable 130 for connecting the controller board 114 (e.g., via a connector) to the power source 120 shown in FIG. 2. The controller board 114 also includes one or more power supplies (not shown) for powering the excitation source 158 in the sensor head 102. In some embodiments the controller board 114 includes a real-time clock battery, a lock-in amplifier, a reference photodetector amplifier, and connectors for the display board 116, the emitter module 140, and the detector module 150. In some cases, the controller board 114 may also have a USB or other type of connector, connection devices (e.g., Ethernet card, wireless adapter, cellular adapter and the like) for communicating with other computing devices.

Figure 3:
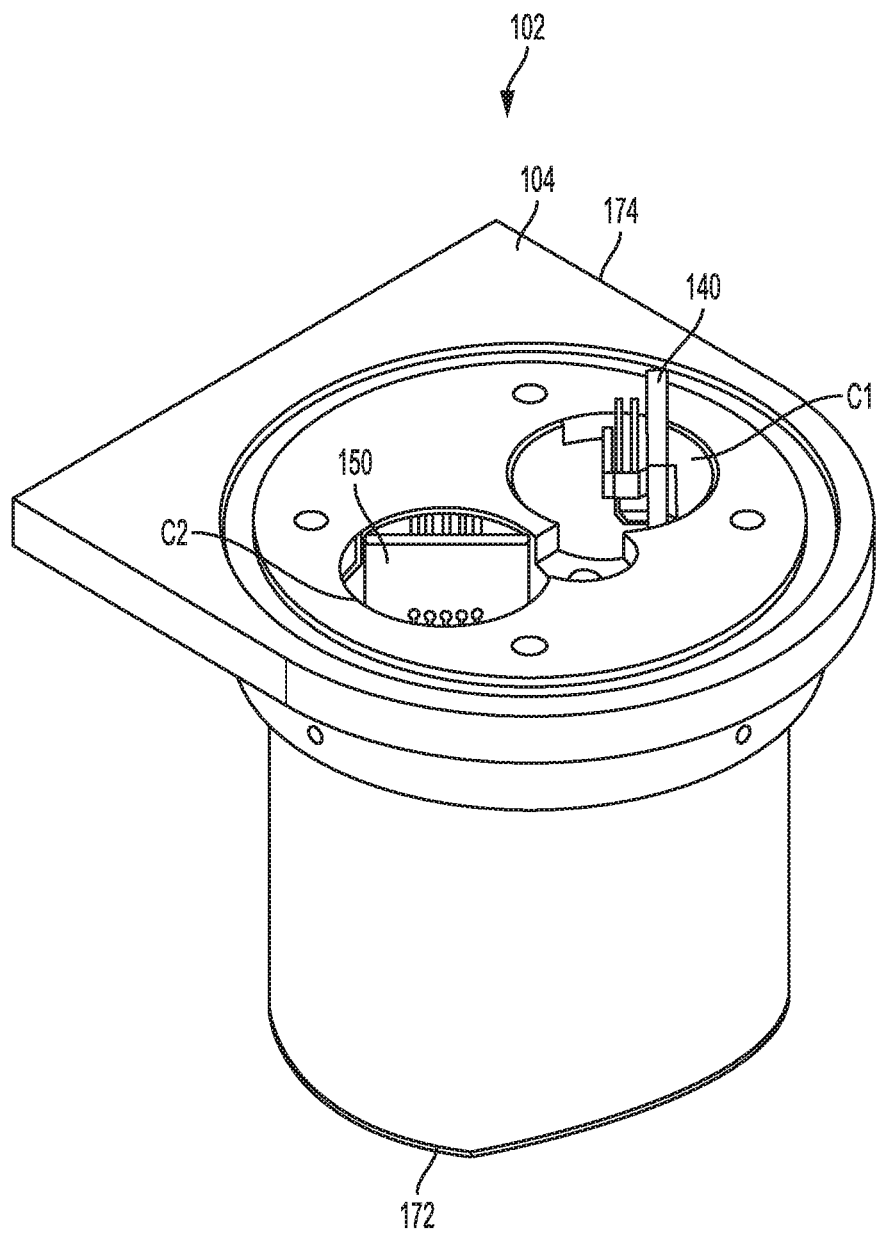
FIG. 3 is a perspective view of a sensor head of a fluorometer according to an embodiment of the invention.
Figure 4:
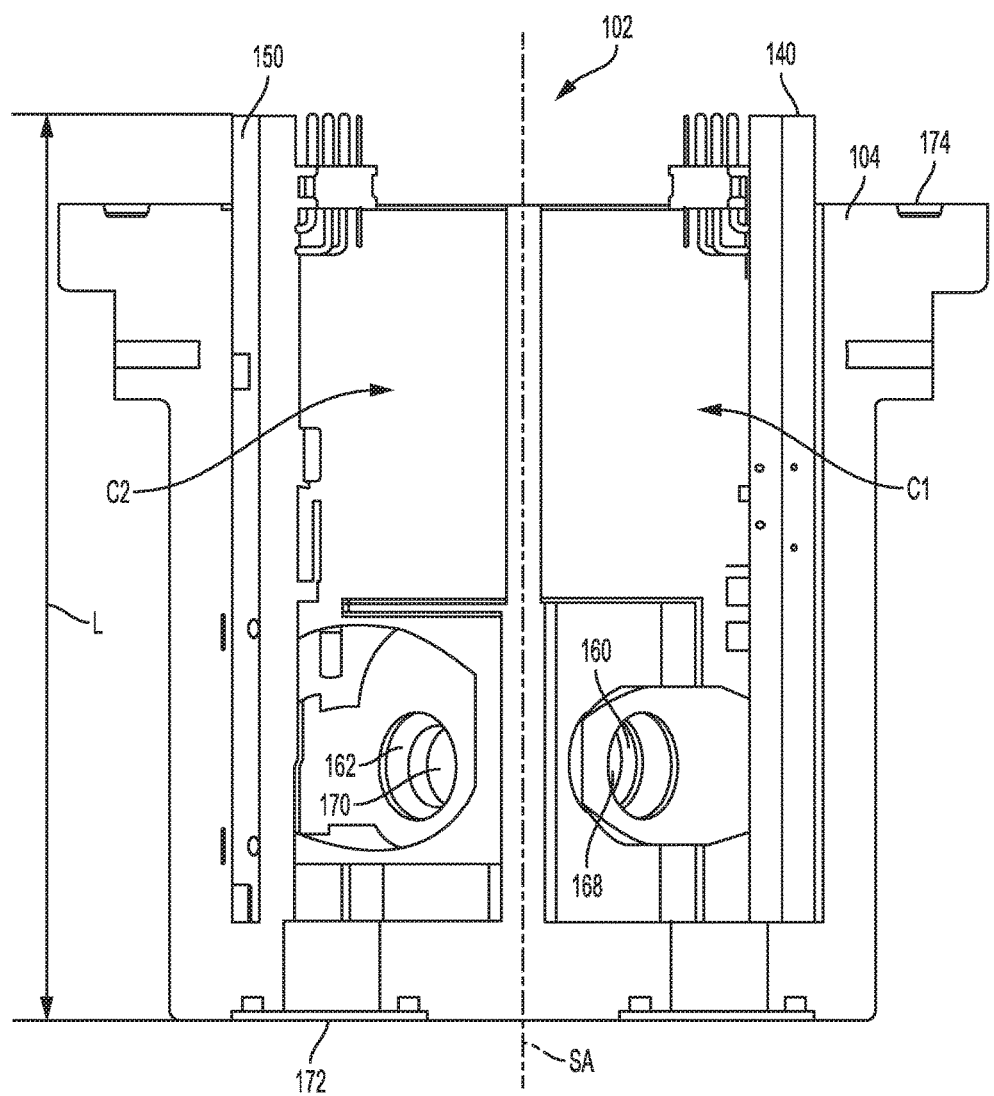
FIG. 4 is a cross-sectional front view of the sensor head of FIG. 3 taken along the sectional plane A-A.
Figure 5:
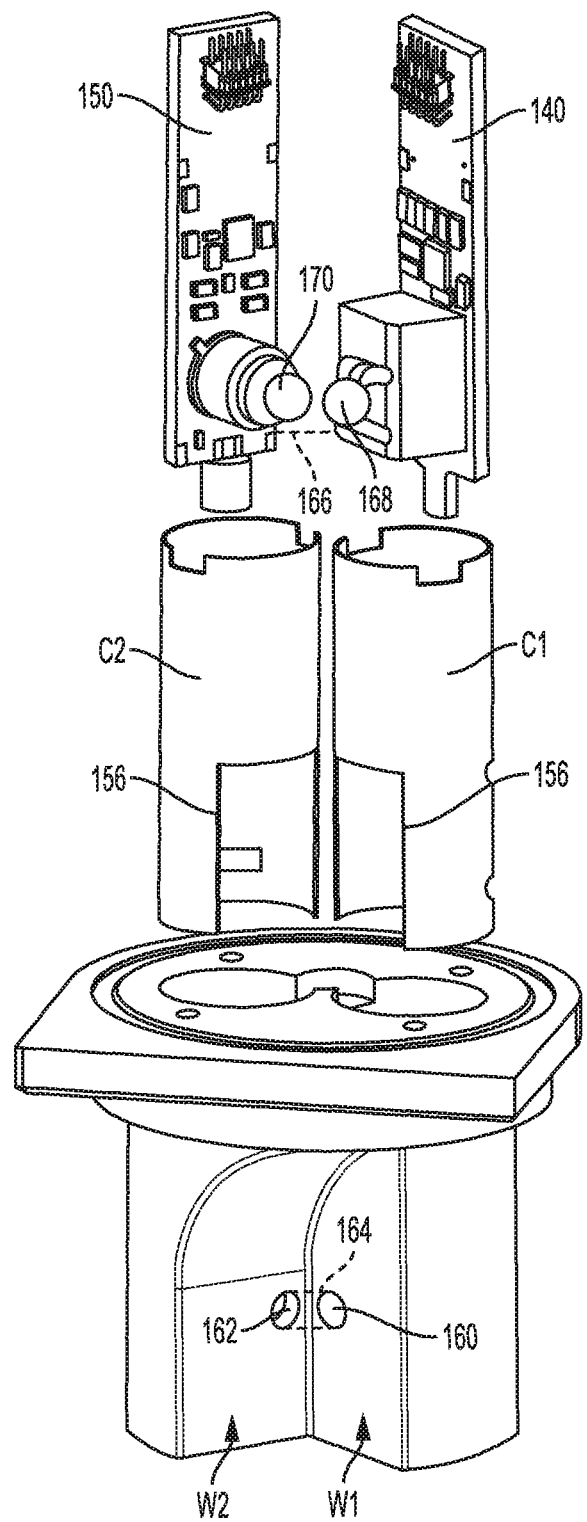
FIG. 5 is an exploded perspective view of the sensor head of FIG. 3.

In some embodiments the sensor head 102 has one or more features and/or components similar to those described in commonly-assigned U.S. Pat. No. 7,550,746 and U.S. Pat. No. 8,084,756, the disclosure of each of which is hereby incorporated herein by reference. Referring now to FIGS. 3 and 4, in some embodiments, the sensor head housing 104 houses an emitter module 140 (best seen in FIGS. 6 and 7) and a detector module 150 (best seen in FIG. 8). The components on the emitter module 140 and the detector module 150 can be held in chambers "C1" and "C2" that encloses each board, as seen in FIG. 5. The first chamber "C1" receives the emitter module 140. The first chamber "C1" can be of cylindrical shape. The second chamber "C2" receives the detector module 150. In some cases, the first chamber C1 and the second chamber C2 may be positioned symmetrically about the longitudinal axis "SA" of the sensor head 102 (e.g., with a vertical orientation). Each chamber "C1" and "C2" includes a cutout, and the sensor head housing 104 extending through the housing. These cutouts 156 allow electromagnetic radiation from an excitation source 158 (e.g., from an LED source) positioned on the emitter module 140 and an emission detector 194 (e.g., phototransistor) positioned on the detector module 150 to communicate with an analytical area outside the sensor head housing 104. Electrical cables couple the emitter module 140 and the detector module 150 to the controller board 114, which allows the controller on the controller board 114 (shown in FIG. 2) to control the excitation source 158 and receive signals back from the emission detector 194. While not illustrated, in some embodiments the sensor head 102 also includes one or more temperature sensors that are able to measure the temperature of a water sample. For example, the emitter module 140 and/or the detector module 150 may include one or more temperature sensors that extend into the sensor head housing 104.

With continued reference to FIG. 5, the excitation window 160 provides a path through a first wall "W1" for the electromagnetic radiation emitted by the excitation source 158. A second wall "W2" similarly defines an emission detector window 162 that provides a path through the second wall "W2" for electromagnetic radiation emitted by the sample to reach the emission detector 194. In some embodiments, the excitation window 160 and/or the emission detector window 162 define a channel 164 extending through the sensor head housing 104. A focusing apparatus 166 may be positioned adjacent each window to prevent electromagnetic radiation from the excitation source 158 (e.g., directed toward the sample), or that emitted by the sample (e.g., toward the emission detector 194) from entering the channel 164. The focusing apparatus 166 can be a lens, mirror, prism or other optical elements known in the art for redirecting electromagnetic radiation. In some embodiments, the focusing apparatus 166 (e.g., ball lenses) is made of glass. For instance, in the illustrated embodiment shown in FIGS. 3-5, a pair of ball lenses 168, 170 is positioned adjacent the excitation and emission detector 194 window. In the illustrated embodiment, the focusing apparatus 166 (e.g., ball lenses) is made of sapphire. In some embodiments, the focusing apparatus 166 can be (e.g., made of suitable materials) to be substantially transparent to the excitation and/or emission wavelengths. For instance, the first ball lens 168 can be substantially transparent to electromagnetic radiation emitted by the excitation source 158 and the second ball lens 170 can be substantially transparent to electromagnetic radiation emitted by the sample. In some embodiments, both the first and second ball lenses 168, 170 can be substantially transparent to electromagnetic radiation emitted by both the excitation source 158 and the sample. As mentioned previously, the focusing apparatus 166 can direct electromagnetic radiation from the excitation source 158 toward the sample and that from the sample toward the detector module 150. At the same time, the focusing apparatus 166 can prevent any electromagnetic radiation (e.g., from the excitation source 158 and the sample) from entering the channel 164 defined by the excitation window 160 and the emission detector 194 window. In some embodiments the excitation and emission detector windows 160, 162 also include a lens, prism or other material optically transparent to the emissions.

Referring back to FIG. 1, in some embodiments, the sensor head 102 includes a proximal end 172 and a distal end 174, between which extends the longitudinal axis "SA" and a length "L" of the sensor head 102. As shown in FIGS. 1 and 3, in some embodiments the sensor head 102 is connected to the bottom surface 122 of the controller housing 112 at or near the proximal end 172 of the sensor head 102. The sensor head 102 may be positioned and oriented such that the longitudinal axis "SA" of the sensor head 102 forms an angle "A" with a longitudinal axis "CA" of the controller module 110. In some cases the sensor head 102 may be removably or fixedly attached to the controller housing 112 with a fastener (not shown). The fastener can include, but is not limited to, screws, bolts, and/or pins. Alternatively, the sensor head 102 may be fixedly bonded to the controller housing 112 by an adhesive or by welding. In some embodiments the sensor head 102 is secured with four screws that compress an O-ring positioned in a groove between the sensor head 102 and the controller module 110. In some embodiments, the sensor head housing 104 may be integrally formed (e.g., molded) with the controller module 110.

While not illustrated, the sensor head 102 can also include part or all of a fastener that removably fastens a sample container to the sensor head 102. In one example, the fastener may comprise one or more pins positioned about the sensor head housing 104. Corresponding slots on the sample container receive the pins extending form the sensor head 102 housing. In some embodiments the pins and the slots form a bayonet fastener that secures the sample container about the sensor head 102 and also aligns the sample container in a preferred orientation (e.g., rotation, three-dimensional position) about the sensor head 102. Other fasteners (e.g., screw threads, opposing pressure elements, etc.) can also be included. Alternatively, the sample container may engage with the sensor head 102 by a friction fit.

While not illustrated, in some embodiments, the sensor head 102 also includes holes for inserting one or more temperature sensor covers. The temperature sensors (not shown) can sense the temperature of the water sample that can be used to correct concentration determination based on errors due to temperature effects. The sensor head 102 can be an immersible sensor head. In some cases, the sensor head 102 can be partly or wholly immersed in a sample. Accordingly, the sensor head housing 104, controller housing 112, and other components can be sealed (e.g., fluid resistant seals, O-rings and the like) prior to immersion. In addition, the excitation window 160 and emission detector window 162 may also be sealed with O-rings and the like. In some embodiments, the excitation window 160 and emission detector window 162 are sealed due to a pressure fit between the windows, channel 164, and the first and second ball lenses 168, 170 placed within the channel 164.

As discussed above, in some embodiments, fluorescence measurements can be taken by a fluorometer 100 by manually lowering the sensor head 102 into a water sample. For example, a user can grasp the controller module 110 and temporarily dip the sensor head 102 into a liquid sample such that the sensor head 102 is partially or completely immersed in the sample and the sample occupies an analytical area near the sensor head 102 windows. In some embodiments of the invention, the orientation of the attachment between the sensor head 102 and the controller module 110 can be set to provide the fluorometer 100 with a desired inclined position on the support surface. For example, as mentioned previously, the sensor head 102 is connected to the controller module 110 such that the longitudinal axis "SA" of the sensor head 102 forms an angle "A" in the range between about 60 degrees and about 90 degrees with the longitudinal axis "CA" of the controller module 110.

Figure 6:
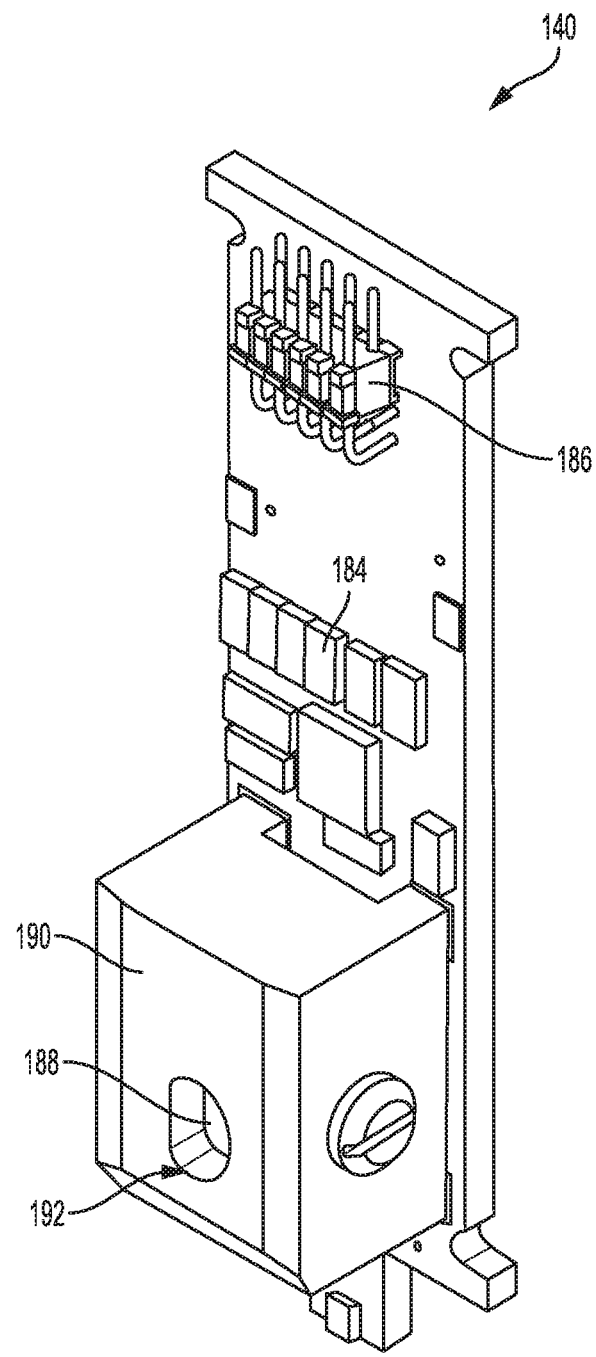
FIG. 6 is a perspective view of an emitter module of a fluorometer according to an embodiment of the invention.
Figure 7:
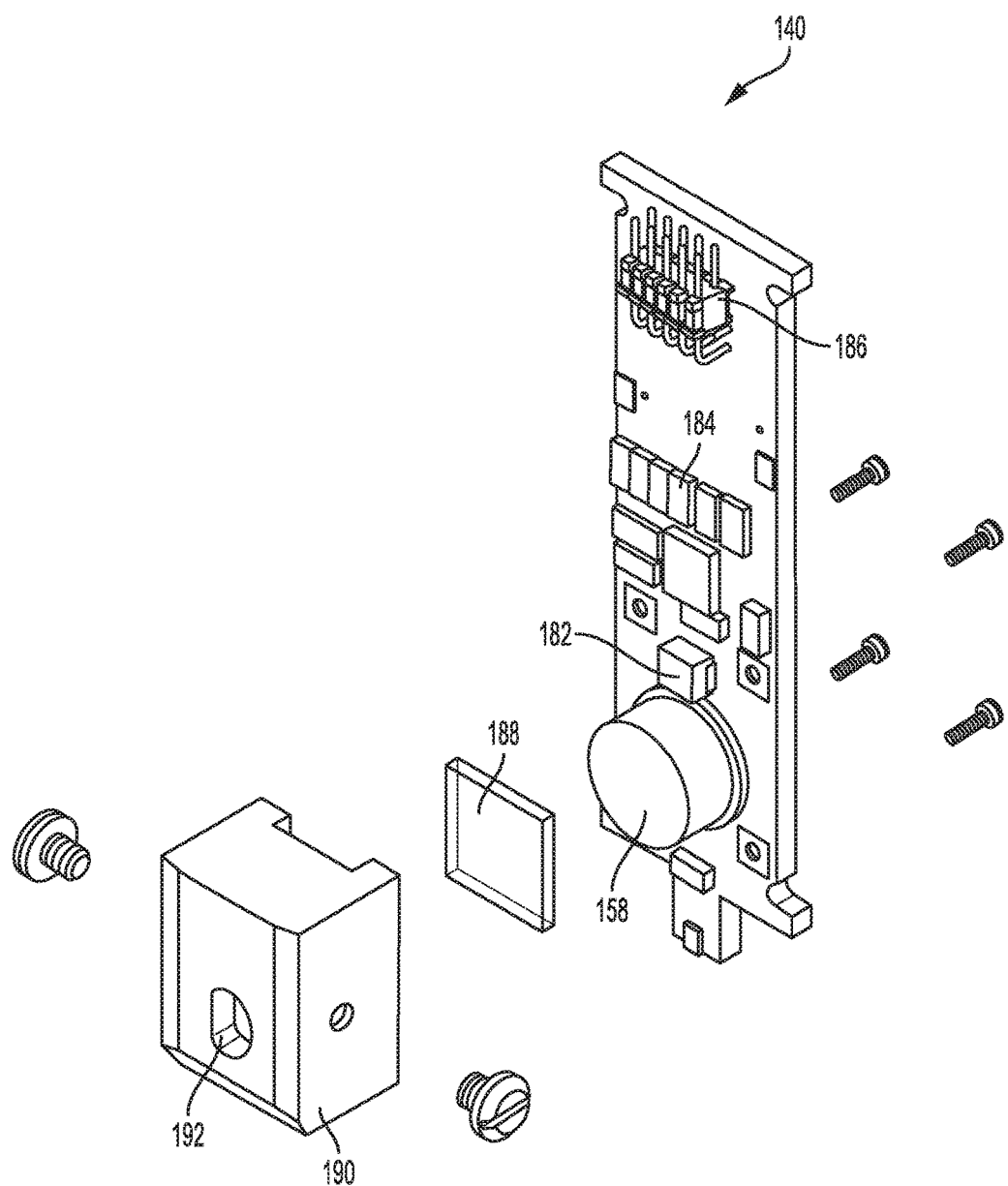
FIG. 7 is an exploded perspective view of the emitter module of FIG. 6.

FIGS. 6 and 7 show various views of an emitter module 140 according to some embodiments of the invention. As best seen in FIG. 7, the emitter module 140 (also shown in FIG. 2 as 320) can include a printed circuit board having an excitation source 158 and a reference photodetector 182 (best seen in FIG. 13). Optionally, the emitter module 140 can include an amplifier 184 and a connector for coupling the emitter module 140 with the controller board 114. The excitation source 158 can include a variety of possible elements. For example, excitation source 158 may be a gas discharge lamp, a mercury lamp, a deuterium lamp, a metal vapor lamp, a light emitting diode (LED) or a plurality of LED lamps. In addition, the excitation source 158 may emit electromagnetic radiation in a number of possible spectrums depending upon the excitation element chosen and the spectrum desired. In some embodiments the excitation source 158 is an LED lamp, capable of emitting ultraviolet (UV) radiation having a wavelength from about 250 nanometers to about 310 nanometers. An excitation filter 188 is positioned in an excitation filter holder 190 to intercept electromagnetic radiation from the excitation source 158. The excitation filter 188 can filter the electromagnetic radiation from the excitation source 158 before it leaves the sensor head 102. The excitation filter holder 190 can define an aperture 192 for passage of electromagnetic radiation from the excitation source 158, via the excitation filter 188 and toward the sample. The shape of aperture 192 may be defined by forming it integrally within the excitation filter holder 190 or it may be defined by forming it via an assembly of components including the excitation filter holder 190.

Figure 9:
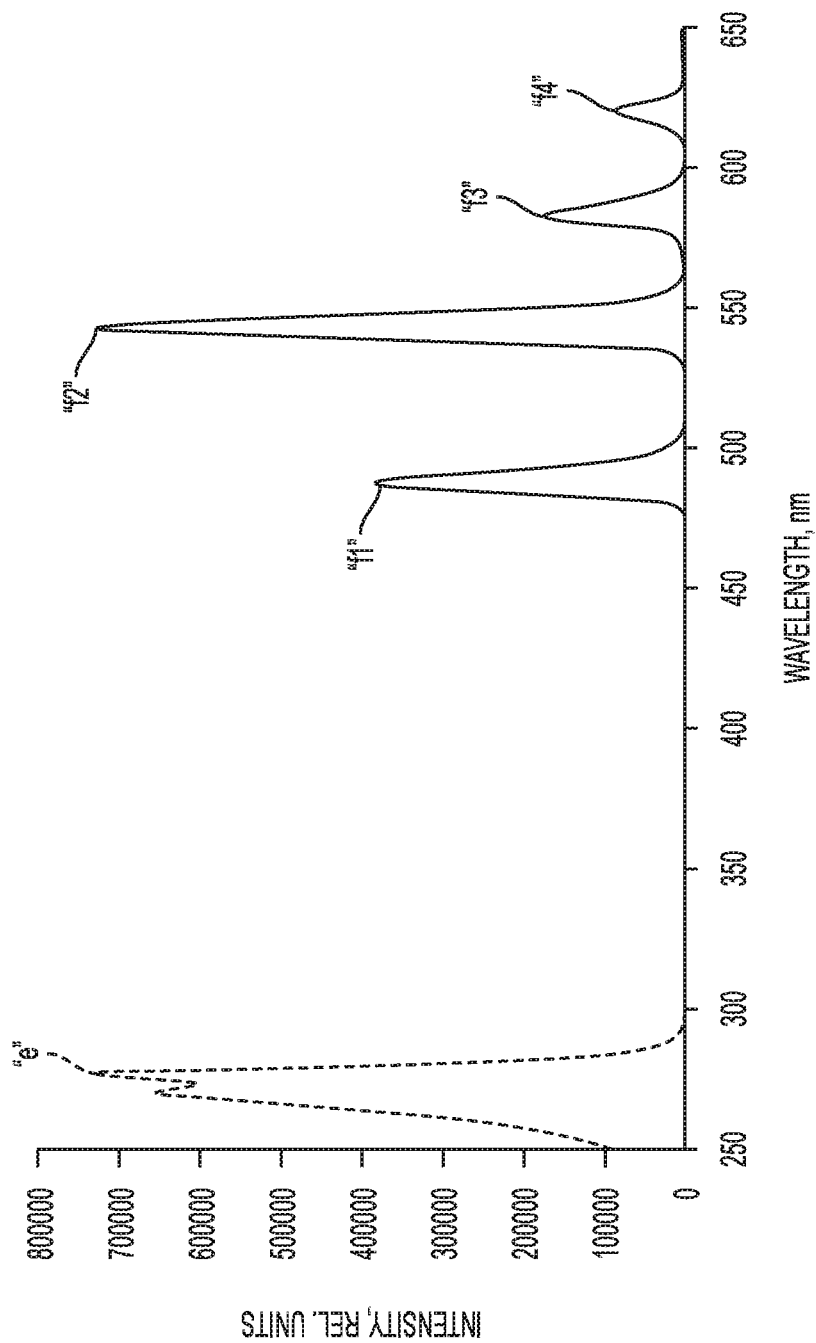
FIG. 9 is a graph showing excitation and fluorescence emission spectrum of the fluorometer according to an embodiment of the invention.
Figure 10A:
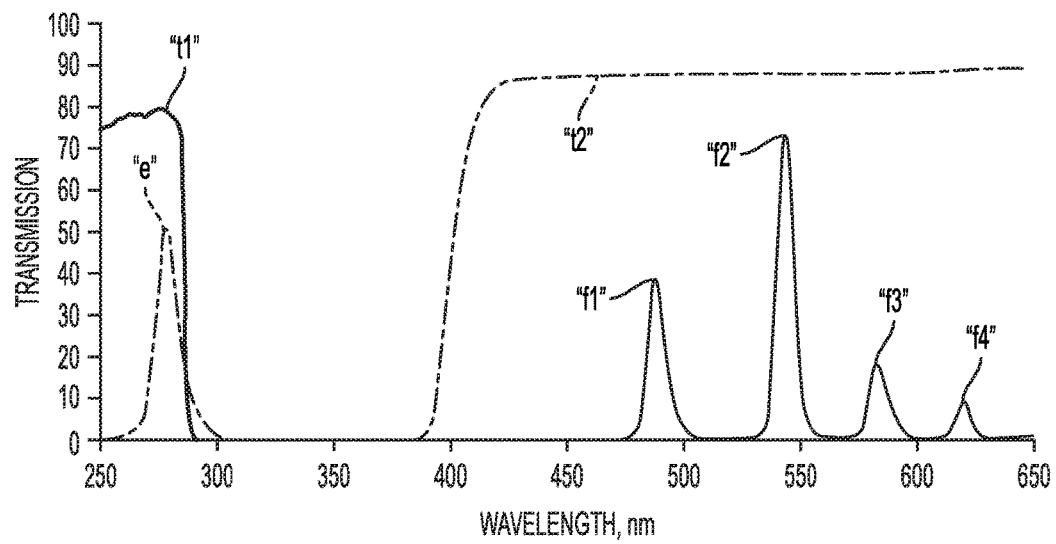
FIG. 10A is a graph showing the transmittance spectra of the excitation and emission filters along with the excitation and fluorescence emission spectra according to an embodiment of the invention.

The excitation filter 188 can substantially transmit electromagnetic radiation from the excitation source 158. In some embodiments, the excitation filter 188 configured for transmitting electromagnetic radiation within a desired wavelength range toward the sample. Referring now to FIGS. 9 and 10, the excitation source 158 can emit electromagnetic radiation at a desired wavelength or in a wavelength range. In the embodiment illustrated in FIG. 6, the excitation source 158 emits electromagnetic radiation in the spectral range between about 250 nanometers and about 300 nanometers. For instance, if fluorescence of dipicolinic acid is to be measured, the excitation source 158 can emit electromagnetic radiation in the spectral range between about 260 nanometers and about 285 nanometers. Optionally, an operator may enter (e.g., via the keypad 108) one or more wavelengths at which electromagnetic radiation is to be emitted by the excitation source 158. The controller 128 may then communicate with the emitter module 140 so that the excitation source 158 emits electromagnetic radiation at the wavelengths selected by the operator. The excitation filter 188 can substantially transmit at least a portion of the electromagnetic radiation in at least a portion of the excitation spectrum (e.g., excitation peak "e" shown in FIG. 9). For instance, the excitation filter 188 can have a transmittance "t1" of between about 50% and about 100% in the spectral range corresponding to excitation. In the illustrated embodiments shown in FIGS. 9 and 10, the excitation filter 188 has a transmittance "t1" of about 75% in the spectral range of between about 250 nanometers and about 285 nanometers. However, other filters having transmittance in a spectrum encompassing the excitation spectrum can also be used. In one example, the excitation filter 188 can have a transmittance "t1" of between about 50% and about 100% in the spectral range of between about 150 nanometers and 380 nanometers, for excitation in the spectral range of between about 250 nanometers and about 300 nanometers. The filtered electromagnetic radiation can then be directed (e.g., by the focusing apparatus 166 shown in FIGS. 4 and 5) toward the sample to induce fluorescent emissions from the sample.

Figure 8:
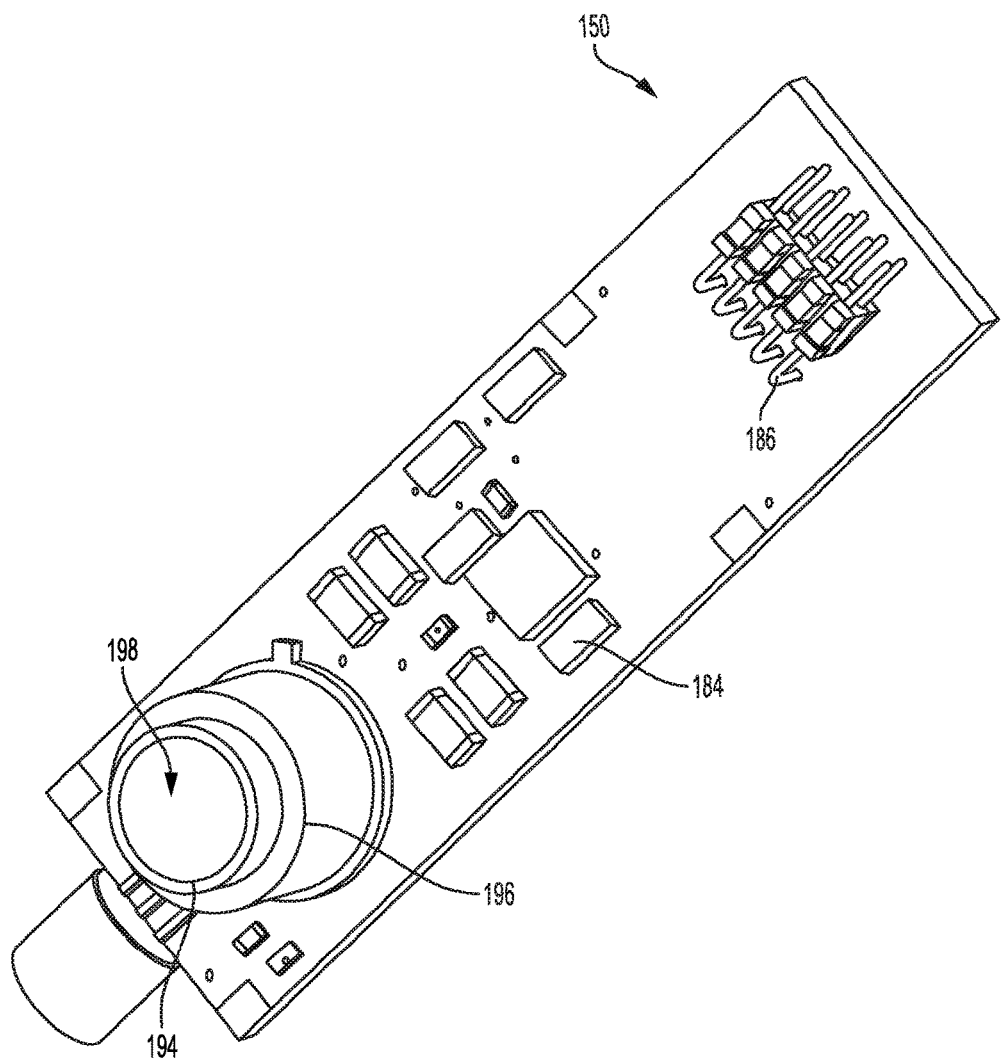
FIG. 8 is a perspective view of a detector module of a fluorometer according to an embodiment of the invention.

FIG. 8 is a perspective view of a detector module 150 according to some embodiments of the invention. The detector module 150 can be used for detecting (e.g., measuring the intensity of) the fluorescence emitted by the sample. The detector module 150 generally includes a number of components, including an emission detector 194 positioned on a printed circuit board. Optionally, the detector module 150 also includes an amplifier 184 and a temperature sensor. The emission detector 194 can be a photodiode. Alternatively the emission detector 194 can be a phototransistor. In some embodiments, the emission detector 194 can sense electromagnetic radiation emitted by the sample at a plurality of wavelengths. In one example, the emission detector 194 can sense electromagnetic radiation at wavelengths between about 400 nanometers and about 1500 nanometers. In the illustrated embodiment shown in FIGS. 9 and 10, the sample emits fluorescence in the spectral range between about 400 nanometers and about 700 nanometers. The sample may emit discretely (e.g., discrete intensity peaks, "f1", "f2", "f3", and "f4" shown in FIG. 9) at selected wavelengths (e.g., about 490 nanometers, about 550 nanometers, about 580 nanometers, and about 620 nanometers). The emission detector 194 can be sensitive to fluorescence emitted by the sample at such discrete wavelengths, and have sufficient linearity (e.g., measured signal linearly proportional to intensity of fluorescence.)

Figure 10B:
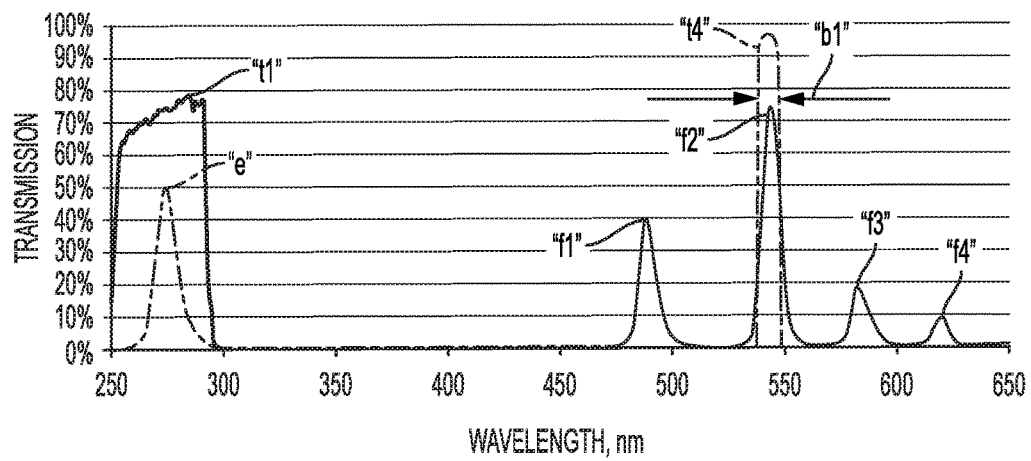
FIG. 10B is a graph showing the transmittance spectra of the excitation and emission filters along with the excitation and fluorescence emission spectra according to another embodiment of the invention.

An emission filter holder 196 positioned about the emission detector 194 supports one or more emission filters 198 for filtering undesirable electromagnetic radiation and transmitting the desired electromagnetic radiation to the emission detector 194. In the embodiment shown in FIG. 8, the emission filter 198 is a polycarbonate filter a thickness between about 1 millimeter and about 10 millimeters. In some embodiments, the thickness of the emission filter 198 can be between about 2 millimeters and about 4 millimeters. The emission filter 198 can be of any shape (square, rectangular, elliptical) and in the illustrated embodiment is of circular shape. Alternatively other filters (e.g., interference glass) filters can be used. Any suitable emission filters transmitting electromagnetic radiation emitted by the sample toward the emission detector 194, and not transmitting (e.g., reflecting or absorbing) electromagnetic radiation at wavelengths other than those emitted by the sample can be used without loss of functionality. The emission filter 198 can have a transmittance "t2" of between about 60% and about 100% in the spectral range corresponding to fluorescence emitted by the sample. In the embodiments shown in FIG. 10A, the emission filter 198 has a transmittance "t2" of about 87% in the spectral range between about 400 nanometers and about 650 nanometers, thereby substantially transmitting the fluorescence emitted by the sample toward the emission detector 194. In some embodiments the sensitivity of fluorescence measurements can be improved and any background signals from other components in chemical composition can be decreased by providing an interference filter as the emission filter 198. In one example shown in FIG. 10B a narrow band interference filter is used as emission filter 198, and a short pass interference filter is used as the excitation filter 188. The short pass interference filter used as the excitation filter 188 can be FF01-300-SP made by Semrock Inc. (Lake Forest, Ill.) and has a transmittance "t3" as shown in FIG. 10B. The narrow band interference filter used as the emission filter 198 can be FF01-543-3 made by Semrock Inc. (Lake Forest, Ill.) and has a transmittance "t4" shown in FIG. 10B. The narrow band interference can have a bandwidth "b1". In the illustrated embodiment shown in FIG. 10B, the bandwidth "b1" can correspond to the wavelength interval over which the narrow band interference filter substantially transmits (e.g., with a transmittance of at least 60%) the electromagnetic radiation emitted by the sample. The bandwidth of the narrow band interference filter can be between about 1 nanometer and 20 nanometers. In the illustrated embodiment, the narrow band interference filter has a bandwidth between about 2 nanometers and about 10 nanometers. Such filters can block as much as 20 times any electromagnetic radiation from background components than other filters known in the art enabling an operator to measure concentrations of DPA lower than 0.1 parts per billion.

The emitter module 140 can be oriented and positioned so that the amount of electromagnetic radiation from the excitation source 158 directed toward the detector module 150 (e.g., via the channel 164 defined by the excitation window 160 and the emission window) is reduced. Referring now to FIGS. 11 and 12A-12D, in some embodiments, the excitation filter holder 190 can be shaped and oriented to prevent electromagnetic radiation from the excitation source 158 from entering the detector module 150, thereby preventing inaccurate measurement of fluorescence emitted by the sample. In some embodiments, the excitation filter holder 190 can permit passage of electromagnetic radiation (e.g., filtered by the excitation filter 188) through the aperture 192 and towards the sample such that the first beam path defines a trajectory of electromagnetic radiation from the excitation source 158 to the excitation filter 188, via the aperture 192 and toward the sample. The aperture 192 can be positioned asymmetrically relative to the first beam path such that the aperture 192 allows a first asymmetrical portion of the electromagnetic radiation in the first beam path to pass therethrough and the excitation filter holder 190 blocks passage of a corresponding second asymmetrical portion of the electromagnetic radiation in the first beam path. The blocked passage of the corresponding second asymmetrical portion of the electromagnetic radiation in the first beam path can reduce the amount of electromagnetic radiation oriented directly from the emitter module 140 to the detector module 150.

In one example, the aperture 192 defined by the excitation filter holder 190 can be of a truncated circular shape, as shown in FIGS. 11 and 12A-12D. For instance, the excitation filter holder 190 can be of semi-circular shape. Alternatively, the aperture 192 can be of other asymmetric shapes (e.g., truncated ellipse, rectangle, triangular or square). The truncated circular shape can substantially direct the filtered electromagnetic radiation from the excitation source 158 toward the sample. The truncated circular shape has a first portion "b" and a second portion "c" In this example, the first beam path is from the excitation source 158 toward the sample, and the trajectory of the beam is from the excitation source 158 to the excitation filter 188. The first asymmetrical portion of the electromagnetic radiation corresponds to electromagnetic radiation directed toward the sample by portion "b", and the corresponding second asymmetric portion of the electromagnetic radiation blocked is that portion of the electromagnetic radiation from the excitation source 158 blocked by the portion "c".

Figure 11:
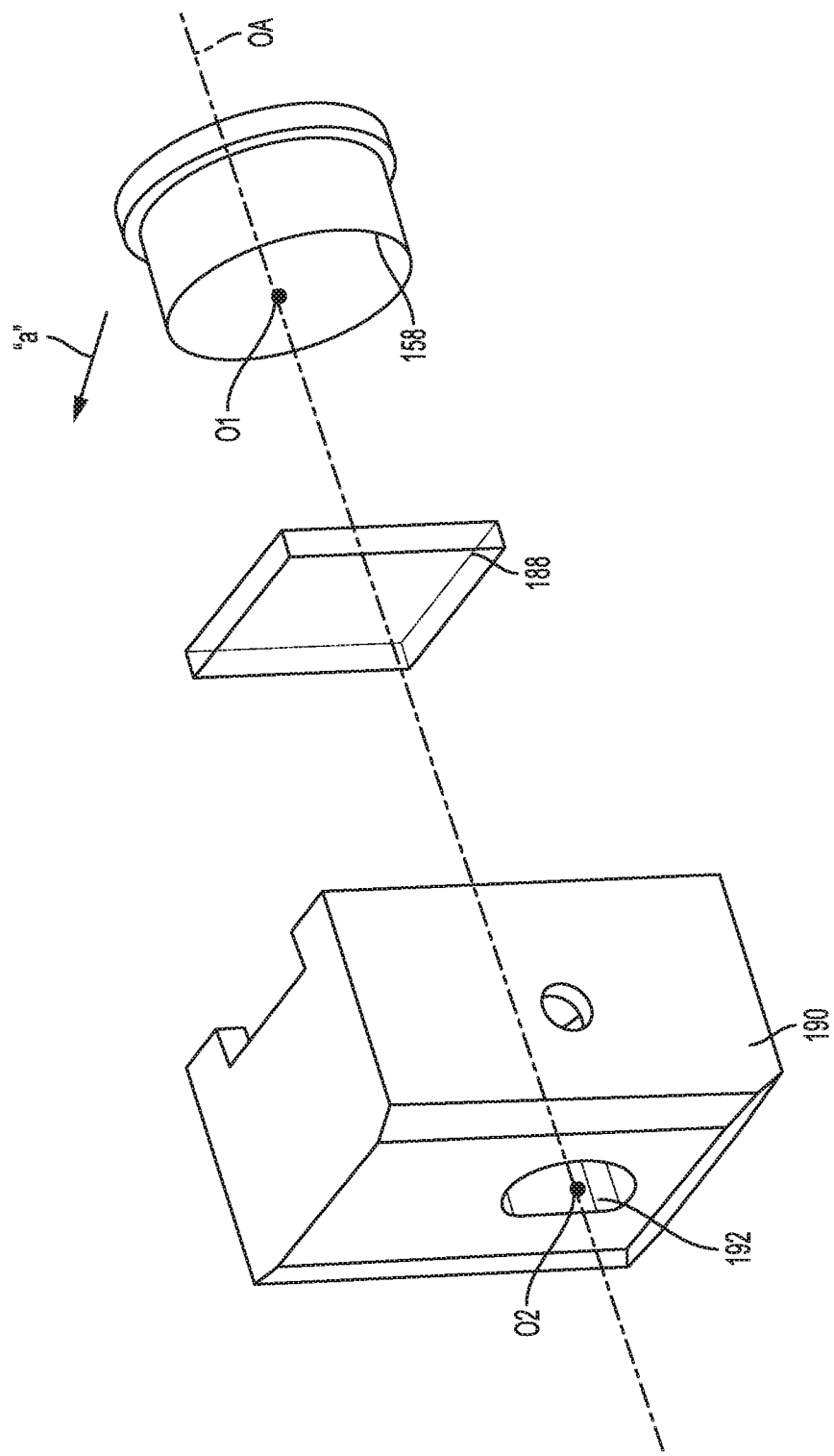
FIG. 11 is a perspective view of a portion of the emitter module of FIG. 3 according to an embodiment of the invention.
Figure 12A:
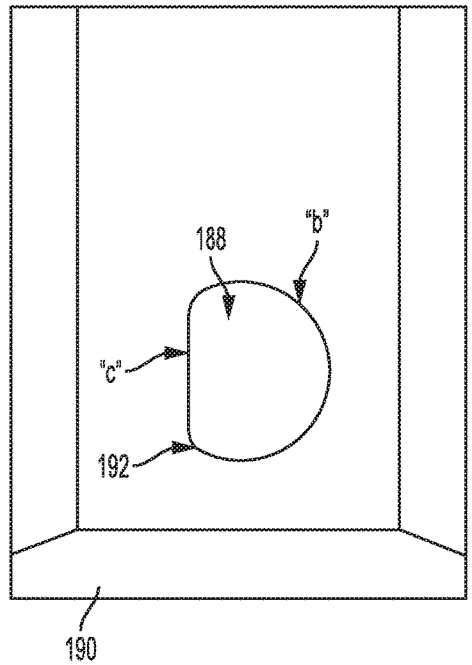
FIG. 12A-12D are front views of a portion of the emitter module according to various embodiments of the invention.
Figure 12B:
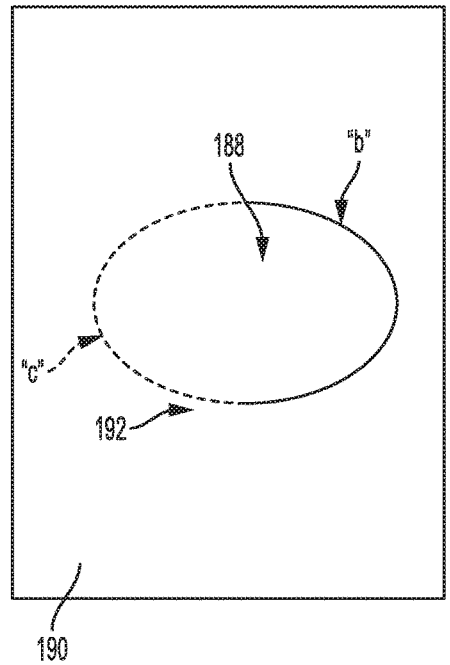
Figure 12C:
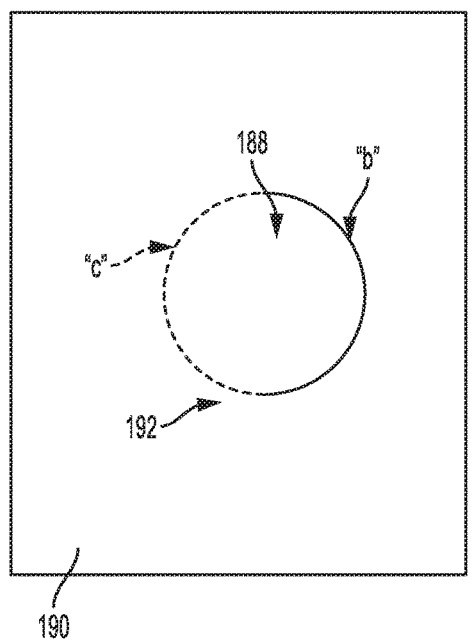
Figure 12D:
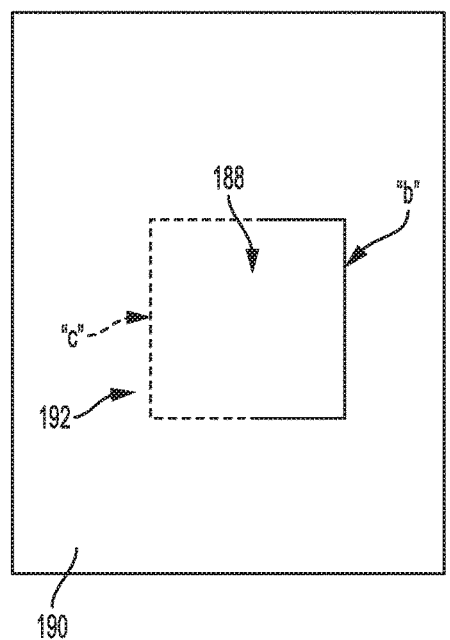

Additionally, or alternatively, the excitation source 158 can be moved from its optical alignment (e.g., along an optical axis "OA" as seen in FIG. 11) with the aperture 192 to an asymmetric position. For instance, as seen in FIG. 11, the geometric center "O1" of the excitation source 158, and the geometric center "O2" of the aperture 192 can be laterally offset with respect to each other from their alignment shown in FIG. 11. In the illustrated embodiment shown in FIG. 11, for instance, if the excitation source 158 is moved further toward the direction "a", nearly all the radiation emitted by the excitation source 158 can be directed toward the portion "b" of the aperture 192 and further toward the sample. This can result in reduced amount of electromagnetic radiation going into other directions. The radiation directed toward portion "b" of the aperture 192 may then be directed by the focusing apparatus 166 toward the sample. Consequently, the amount of electromagnetic radiation reaching the detector module 150 can be reduced. In this case, the first asymmetrical portion of the electromagnetic radiation is that which is toward the sample via portion "b", while the corresponding second asymmetrical portion may refer to any electromagnetic radiation not directed toward the portion "b" of the aperture 192. In some cases, the corresponding second asymmetrical portions may equal zero, corresponding to a state where no electromagnetic radiation is directed in a direction other than a direction toward the sample.

Figure 13:
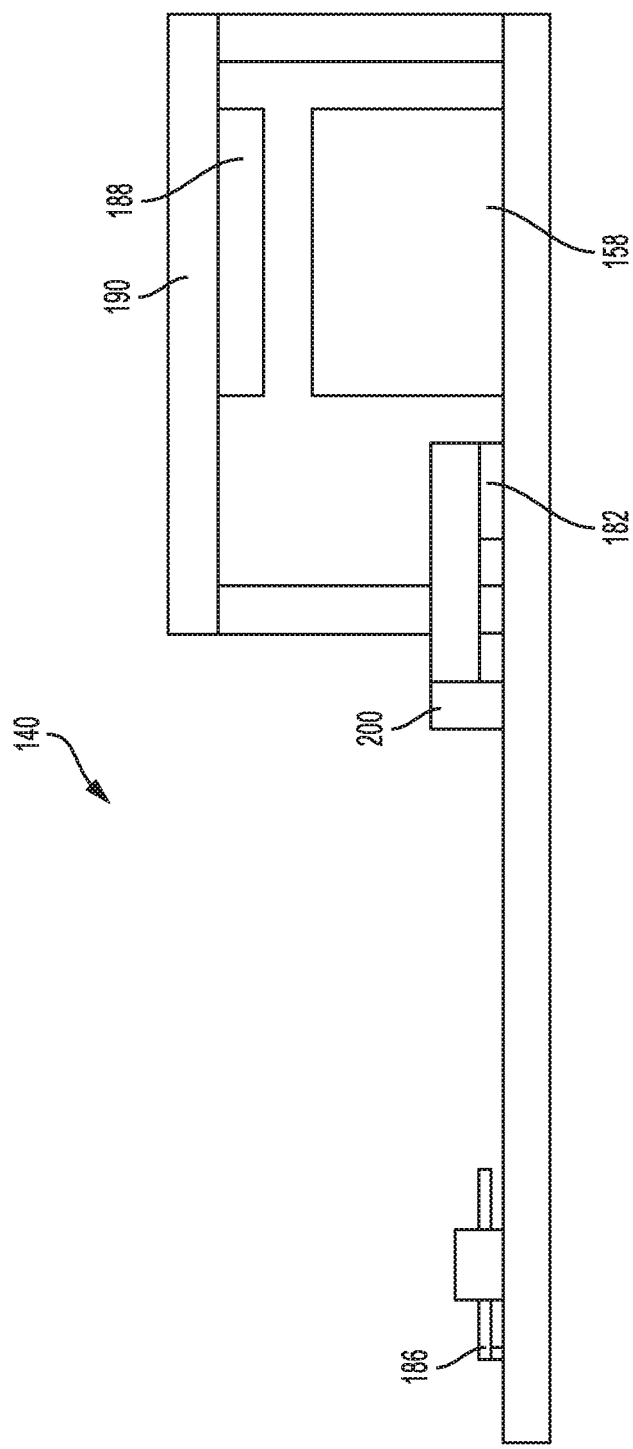
FIG. 13 is a side view of an emitter module according to another embodiment of the invention.

In certain embodiments, the sensitivity of the fluorometer 100 can be improved by reducing the intensity of stray electromagnetic radiation. One source of such stray electromagnetic radiation can be those that are reflected by internal surfaces of the excitation filter holder 190. Electromagnetic radiation from the excitation source 158 may reach the walls of the excitation filter holder 190 (via the excitation filter 188). The walls of the excitation filter holder 190 may reflect the electromagnetic radiation toward areas in the emitter module 140 that lead to reduced measurement sensitivity. For instance, as seen in FIG. 13, a reference photodetector 182 may be placed on the emitter module 140 to monitor the intensity of the electromagnetic radiation emitted by the excitation source 158. The intensity of the electromagnetic radiation emitted by the excitation source 158 can be useful in determining the concentration of the sample. Stray electromagnetic radiation (e.g., reflected by the excitation filter holder 190) may reach the reference photodetector 182, and result in the reference photodetector 182 being saturated. To prevent the reference photodetector 182 from being saturated, an attenuator 200 may be placed on a least a portion of the reference photodetector 182. The attenuator 200 can obstruct at least a portion of the reference photodetector 182. The attenuator 200 can provide spatially uniform attenuation of electromagnetic radiation emitted by the excitation source 158 over a surface area of the attenuator 200 such that the attenuator 200 helps prevent the reference photodetector 182 from being saturated with electromagnetic radiation. In some embodiments best seen in FIG. 13, the attenuator 200 can include a layer of polytetrafluoroethylene (Teflon) coupled (e.g., bonded by an adhesive) to the emitter module 140. Alternatively, the attenuator 200 can be made of stainless steel mesh. The attenuator 200 can be coupled to the emitter module 140 in any manner (e.g., with a fastener, adhesive, by welding, soldering, thermally-treating etc.). In some embodiments, the thickness of the attenuator 200 can be between about 0.1 millimeter and 1 millimeter. For instance, the attenuator 200 can be a layer of Teflon of thickness of about 0.5 millimeters (20 mil). Once the reflections are attenuated, the reference photodetector 182 does not become saturated with electromagnetic radiation, thereby facilitating improved sensitivity and accuracy of measurement.

Embodiments of the invention are thus useful in many applications. Fluorometers according to some embodiments of the invention are suitable for bacterial spore detection by adding terbium chloride to microbial spore (e.g., bacterial spore, which may comprise dipicolinic acid). The dipicolinic acid and terbium chloride solution may produce fluorescence intensity linearly proportional to the concentration, thereby enhancing the sensitivity of concentration and/or fluorescent measurement. Embodiments of the invention also provide enhanced sensitivity due in part to the immediate proximity of the sample to the excitation source and the emission detector. Embodiments of the invention facilitate low cost elimination of stray electromagnetic radiation, and improved measurement sensitivity. Better accuracy in measuring even low intensity fluorescence can facilitate measuring very low concentrations of product (e.g., parts per billion, ppb) and/or for measuring concentrations of product in a colored sample and/or those with turbidity.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention.

What is claimed is:

1. A method of detecting concentration of dipicolinic acid in a chemical composition, comprising:
    adding terbium chloride to a sample of the chemical composition to form a resulting chemical composition wherein the terbium chloride combines with the dipicolinic acid in the resulting chemical composition;
    providing a fluorometer, comprising:
        an excitation source,
        an excitation filter,
        an excitation filter holder defining an aperture positioned asymmetrically relative to a first beam path, and
        a detector for detecting fluorescence emitted by dipicolinic acid;
    emitting, via the excitation source, electromagnetic radiation,
    filtering, via the excitation filter, the electromagnetic radiation emitted by the excitation source to within a first wavelength range, the first wavelength range corresponding to wavelengths that induce fluorescence in the dipicolinic acid terbium chloride combination present in the resulting chemical composition;
    permitting passage of filtered electromagnetic radiation through the aperture and towards the resulting chemical composition along the first beam path such that the first beam path defines a trajectory of electromagnetic radiation from the excitation source to the excitation filter, via the aperture and toward the resulting chemical composition,
    wherein the aperture passes an asymmetrical portion of the electromagnetic radiation in the first beam path;
    blocking, via the excitation filter holder, passage of a corresponding asymmetrical portion of the electromagnetic radiation in the first beam path,
    the blocking of passage of the corresponding asymmetrical portion of the electromagnetic radiation in the first beam path reducing the amount of electromagnetic radiation oriented directly from the excitation source to the detector;
    detecting, via the detector, the fluorescence emitted by the dipicolinic acid-terbium chloride combination; and
    determining the concentration of dipicolinic acid in the resulting chemical composition using a predetermined relationship between fluorescence emitted and the concentration of the dipicolinic acid-terbium chloride combination in the resulting chemical composition.

2. The method of claim 1, wherein the predetermined relationship between fluorescence and concentration of the dipicolinic acid-terbium chloride combination is linear.

3. The method of claim 1, wherein dipicolinic acid is present in the chemical composition in concentrations such that the chemical composition is stable.

4. The method of claim 1, further comprising, emitting electromagnetic radiation in the spectral range between about 260 nanometers and about 285 nanometers to induce fluorescence in the dipicolinic acid-terbium chloride combination.

5. The method of claim 4, further comprising, emitting electromagnetic radiation at a wavelength of about 275 nanometers to induce fluorescence in the dipicolinic acid-terbium chloride combination.

6. The method of claim 1, further comprising, detecting fluorescence in a spectral range between about 400 nanometers and about 700 nanometers.

7. The method of claim 6, wherein the resulting chemical composition emits fluorescence in the spectral range between about 400 nanometers and about 700 nanometers.

8. The method of claim 7, wherein the resulting chemical composition emits fluorescence discretely in the spectral range between about 400 nanometers and about 700 nanometers.

9. The method of claim 8, wherein the resulting chemical composition emits fluorescence at discrete wavelengths of about 490 nanometers, about 550 nanometers, about 580 nanometers, and about 620 nanometers.

10. The method of claim 9, wherein intensity of fluorescence at about 550 nanometers is greater than intensities of fluorescence at wavelengths about 490 nanometers, about 580 nanometers, and about 620 nanometers.

11. The method of claim 1, wherein the fluorometer is handheld.

12. A method of detecting concentration of dipicolinic acid in a chemical composition, comprising:
    preparing a stable chemical composition comprising dipicolinic acid and terbium chloride;
    providing a fluorometer, comprising:
        an excitation source,
        an excitation filter,
        an excitation filter holder defining an aperture positioned asymmetrically relative to a first beam path, and
        a detector for detecting fluorescence emitted by the chemical composition;
    emitting, via the excitation source, electromagnetic radiation;
    filtering the electromagnetic radiation emitted by the excitation source to within a first wavelength range, the first wavelength range corresponding to wavelengths that induce fluorescence in the chemical composition;
    permitting passage of filtered electromagnetic radiation through the aperture and towards the chemical composition along the first beam path such that the first beam path defines a trajectory of electromagnetic radiation from the excitation source to the excitation filter, via the aperture and toward the chemical composition,
    wherein the aperture passes an asymmetrical portion of the electromagnetic radiation in the first beam path;
    blocking, via the excitation filter holder, passage of a corresponding asymmetrical portion of the electromagnetic radiation in the first beam path,
    the blocking of passage of the corresponding asymmetrical portion of the electromagnetic radiation in the first beam path reducing the amount of electromagnetic radiation oriented directly from the excitation source to the detector;
    detecting the fluorescence discretely emitted by the chemical composition via the detector;
    suppressing transmission of electromagnetic radiation from components other than dipicolinic acid and terbium chloride in the chemical composition; and determining the concentration of dipicolinic acid using a predetermined relationship between fluorescence emitted and the concentration of the dipicolinic acid-terbium chloride combination.

13. The method of claim 12, further comprising, providing an interference filter to selectively transmit electromagnetic radiation at selected wavelengths from the excitation source toward the chemical composition or from the chemical composition toward the detector.

14. The method of claim 13, wherein the interference filter permits passage of electromagnetic radiation at selected wavelengths from the excitation source toward the chemical composition, the selected wavelengths corresponding to wavelengths at which fluorescence is induced in the dipicolinic acid-terbium chloride combination.

15. The method of claim 14, wherein the interference filter permits passage of electromagnetic radiation emitted by the excitation source between wavelength of about 260 nanometers and about 280 nanometers.

16. The method of claim 13, wherein the interference filter permits passage of electromagnetic radiation at selected wavelengths from the chemical composition toward the detector, the selected wavelengths corresponding to wavelengths at which the dipicolinic acid-terbium chloride combination emits fluorescence.

17. The method of claim 16, wherein the interference filter permits passage of electromagnetic radiation at a wavelength of about 550 nanometer from the chemical composition toward the detector.

18. The method of claim 13, wherein the interference filter suppresses transmission of electromagnetic radiation from components other than dipicolinic acid-terbium chloride combination in the chemical composition.

19. The method of claim 12, wherein the fluorometer is handheld.

20. The method of claim 12, wherein the dipicolinic acid is added to the chemical composition.

* * * * *